United States Patent
Horstmann et al.

(10) Patent No.: US 6,800,329 B2
(45) Date of Patent: Oct. 5, 2004

(54) METHOD FOR PRODUCING FILM-TYPE DOSAGE

(75) Inventors: Michael Horstmann, Neuwied (DE); Wolfgang Laux, Diez (DE); Horst Dzekan, Meinborn (DE); Katja Zinndorf, Weitersburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 10/314,549

(22) Filed: Dec. 9, 2002

(65) Prior Publication Data

US 2003/0087034 A1 May 8, 2003

Related U.S. Application Data

(63) Continuation of application No. 09/913,089, filed as application No. PCT/EP00/00739 on Jan. 31, 2000, now abandoned.

(30) Foreign Application Priority Data

Feb. 12, 1999 (DE) .......................................... 199 05 801

(51) Int. Cl.[7] ................................................. B05D 3/02
(52) U.S. Cl. ....................... 427/379; 427/384; 424/443; 424/447
(58) Field of Search ................................ 427/384, 379; 424/443–447, 448, 449

(56) References Cited

U.S. PATENT DOCUMENTS

| | | | | | |
|---|---|---|---|---|---|
| 3,444,858 A | * | 5/1969 | Russsell | ...................... | 604/77 |
| 4,128,445 A | * | 12/1978 | Sturzenegger et al. | ......... | 156/64 |
| 4,197,289 A | * | 4/1980 | Sturzenegger et al. | ...... | 424/443 |
| 4,562,020 A | * | 12/1985 | Hijiya et al. | ................... | 264/39 |
| 5,047,244 A | * | 9/1991 | Sanvordeker et al. | ....... | 424/435 |
| 5,273,760 A | * | 12/1993 | Oshlack et al. | ............. | 424/480 |
| 5,456,745 A | * | 10/1995 | Roreger et al. | .......... | 106/140.1 |
| 5,599,577 A | * | 2/1997 | Stevens et al. | ............ | 427/2.14 |
| 6,143,353 A | * | 11/2000 | Oshlack et al. | ............ | 427/2.21 |

FOREIGN PATENT DOCUMENTS

| | | | |
|---|---|---|---|
| DE | 3333240 | * | 3/1985 |
| DE | 3630603 | * | 3/1988 |
| EP | 275550 | * | 7/1988 |
| EP | 460588 | * | 12/1991 |
| WO | WO 95/29664 | * | 11/1995 |
| WO | WO 98/26764 | * | 6/1998 |

OTHER PUBLICATIONS

Heidemann et al, Pharmaceutical Research, 8(3), pp 292–297, 1991.*

* cited by examiner

*Primary Examiner*—Erma Cameron
(74) *Attorney, Agent, or Firm*—Jordan and Hamburg LLP

(57) ABSTRACT

A process for the production of sheet-like administration forms by way of coating and drying a solvent-containing, spreadable mass on a substrate is characterized in that the drying takes place in a first drying stage at between 30 and 50° C., in a second drying stage at between 35 and 80° C., and in third drying stage at between 25 and 50° C.

12 Claims, No Drawings

METHOD FOR PRODUCING FILM-TYPE DOSAGE

This is a continuation of U.S. patent application Ser. No. 09/913,089, filed Aug. 27, 2001, which is the National stage of International Application No. PCT/EP00/00739 filed Jan. 31, 2000, now abandoned.

The present invention relates to sheet-like administration forms for application as cosmetic, pharmaceutical or food-technological products.

Flat-shaped administration forms for use in the oral region and on the mucous membranes of the mouth are well-known. Thus, U.S. Pat. No. 3,444,858 (Russell, 1969) already describes medicament strips based on a gelatine-like material.

In EP 0 216 762 a water-soluble film of starch, gelatine, glycerine or sorbite is disclosed which is coated employing a roll-coating method. The document shortly mentions in this context that such dosage forms can also be produced for chemical reagents, flavours and the like.

A formulation that is in principal suitable for making sheet-like systems is disclosed in EP 0 460 588. Here, the composition of 20 to 60 percent by weight of film former, 2 to 40% gelatinizing agent, 0.1 t 35 percent by weight of active substance (here: flavouring agent) and a maximum of 40 percent by weight of an inert filler is regarded as affording particular advantages. DE 36 30 603 sees particular advantages in designing the flat-shaped dosage form on a carrier material (release film) so as to peelable in doses.

U.S. Pat. Nos. 4,128,445 and 4,197,289 (Sturzenegger, 1978) address possible technical solutions in connection with the loading with active substances.

For drug-containing sheet-like systems a two-layer structure of a water-swellable layer and a water-insoluble barrier film is also regarded as advantageous (U.S. Pat. No. 5,047,244).

In the manufacture of such films, some hydrophile film formers, especially pullulan and other glucans, but also cellulose derivatives, exhibit insufficient wetting on common coating media. This may result in premature or difficult substrate detachment as well as a resultant uneven film thickness. As a remedy, U.S. Pat. No. 4,562,020 recommends the use of a substrate circulating in the process as a loop, said substrate being based on nonpolar heat-stable polymers and, during the process, being continuously subjected to a superficial corona treatment, thus being constantly provided with a new polar surface that has a sufficiently safe wetting capability. The drying temperatures are between 40 and 110° C.; temperatures mentioned in the Examples are 60 and 85° C.

The aroma films produced on the pure film substrates have proved disadvantageous because of their being smooth on both sides. Such products have only limited suitability for the further processing and use in stacks formed by film cutting. Such stacks of film pieces or punched film pieces, as are frequently offered to the consumer in suitable dosage dispensers, tend to stick to each other, which makes it much more difficult to safely remove the pieces. As such film-shaped administration forms, due to their small weight per unit area (typically approx. 10 to 80 g/m$^2$) tend to become statically charged, and since, at the same time, their surfaces, to facilitate later removal, are designed so as to be slidable on each other, this aspect is disturbing not only in use but also in the process technology.

A third demand that should be met by the process is that loss of flavour due to heat be prevented while affording maximum process rates. The prior art reveals no information pointing towards a solution to this demand.

From these requirements, which have as yet remained unsolved in the prior art, results the object of the present invention of providing processes for making sheet-like active substance carriers which enable a precise and reproducible coating quality, prevent the mutual adhesion of the finally produced pieces of film or sheet in the stack, and can be obtained, while avoiding contamination and excessive thermal load, at high production rates.

This object is achieved according to the present invention in that immediately subsequent to the coating of the solution of hydrophile polymers with added active substances and further auxiliary substances, a stream of moderately warm air (30–50° C.) is passed over the material, whereafter the temperature is raised slightly (35–80° C.), finally followed by a reconditioning phase at 25–50C. The process rate is advantageously regulated such that an equilibrium relative humidity of 50–75%, preferably 60–68%, is maintained in all cases. By using rough-surface substrates, preferably thermoplasts of polypropylene, polyethylene, polyethylene terephthalate, polycarbonate, and laminates of these polymers, with polyethylene-coated paper being particularly preferred, it is effectively prevented that the later-produced single film pieces stick to each other in a stack.

The process according to the invention is applicable to any form of flat-shaped products—for example, for use as a food stuff, medicament or a cosmetic—which can be produced in a coating process from a mass which has been fluidized by solvents, especially water, and contains solid, hydrophile base substances and optionally further components.

These hydrophile base substances may be polymers such as starch and its derivatives, agar-agar, gelatine, cellulose and cellulose derivatives, alginic acid, galactoglucomannan, carragéen, other vegetable gums permitted for the respective field of application, pullulan and other glucans, dextrane, and polyvinylpyrrolidone, polyvinyl alcohol or polyacrylic acid homopolymers and copolymers. The polyvinyl alcohol used is advantageously a partially hydrolised form wherein between 1 and 20%, especially preferred: approximately 12%, of the hydroxyl groups are replaced by acetyl groups.

The process according to the invention is effective in particular with problematic masses containing high portions of pullulan, carrageen or cellulose esters.

Hydrophile additives of small molecular weight may also be employed, as structure-forming agents; these mostly serve to achieve application-specific objects. Possible additives are, inter alia, sugar, sugar alcohols, sugar substitutes, organic acids, polyethylene glycol.

Solid substances which due to their poor solubility do not form a molecular-disperse mixture or solution in the base material may also be contained. Suitable substances are, for example, carbonates, phosphates, silicates, or sulfates of the alkali earth metals, zinc oxide, titanium oxide or other colour pigments, talcum, lactose, cyclodextrins or starch and starch derivatives, as far as they form their own, solid, disperse phase in the final product.

The above list is exemplary only and can be completed by substances of the same function known to those skilled in the art.

Active components may, for example, be medicinal or cosmetic active agents, dietary additives to foods, colourants or diagnostics. In particulars the process according to the invention can be employed with flavouring agents which are otherwise difficult to process because of their volatility. The flavours which may be used with this invention are mainly essential oils (volatile, water-insoluble distillates of fragrant components of plants) and other volatile, fragrant substances having a limited miscibility with water. Examples therefor are phenyl ethanol as a component of rose fragrance aromatics, menthol, eucalyptol (cineole), camphene and pinene in peppermint-like fresh flavourings, appetite inducing flavourings (spicing aromatics) such as, for example, n-butylphthalide or cineole, but also flavours having medicinal applications, such as eucalyptus oil, thyme oil, methyl salicylate, terpentine oil and camomile oil.

A very broad field is taken up by essences and aromatics which are being used as additives in foods, and in prefabricated food additives. Examples for these are the so-called fruit ethers, but also other aromatics such as ethyl vanillin, 6-methylcoumarin, citronellol or n-butyl acetate. Additives of surface-active substances can improve the uniformity of the distribution of the droplets of aromatics. In special cases it may prove to be of advantage to apply one or more further layers of equal or different composition, in order to obtain special surface or tensile properties, for example.

The mass is prepared, for example, by strewing-in, kneading-in or slowly digesting the solid components in the solvent (typically water, but also, e.g., ethanol, acetone and other compatible, physiologically acceptable solvents and mixtures thereof are employed). To this phase is added, while stirring slowly, the pre-weighed amount of flavouring agent and other liquid, lipophile additives, as far as provided by the recipe.

In the interest of the object of the invention, it has turned out to be of great advantage with respect to a uniform constitution to homogenize the mass, prior to coating, on a high-speed homogenizer.

In the process according to the invention, the mass is coated on a substrate using a spread-coating, knife-coating or extrusion method, and is dried in a drying canal consisting of at least three independently temperature-controlled zones.

The substrate may in principle consist of substrates known to those skilled in the art and widely used, such as, for instance, polyethylene terephthalate, polyethylene, polypropylene, polycarbonate, polyurethane. Also used are laminates of these substances with other polymers, paper, fibreglass, and other structure-forming materials for increasing tensile strength. To regulate surface adhesion it may be useful to take measures such as siliconization, fluorination, acid treatment or corona treatment, but these require clarification of their physiological tolerance for the relevant purpose of application in each individual case.

Special advantages are achieved according to the invention if the surface facing towards the coating mass does not have a smooth contour, but a contoured, dulled, and in any case rough-surface contour. The peak-to-valley height can be in the range of 0.1 $\mu$m to about 10 $\mu$m, preferably between 0.5 and 3 $\mu$m. Of advantage are rounded protrusions in the microstructure, which further reduce sliding friction.

The object of the present invention is regularly achieved where the drying takes place at a process temperature which rises initially and is then, in the last zone at the latest, reduced by 10° C.

Advantageously, the process rate is to be adjusted such that a product having an equilibrium relative humidity of 50–75%, preferably 60–68%, is obtained.

Under these process conditions the products obtained proved surface-stable, flexible and break-resistant as well as largely tear-resistant. The resultant surfaces exhibit virtually no "cold flow" and are thus basically dimensionally stable. The film can be removed from the support without perceptible elongation occurring, and can be further processed separately.

The equilibrium relative humidity is determined as follows: A freshly prepared product strip of about 0.1 m$^2$ in area is immediately and quickly folded, using rubber gloves, and placed in a wide-neck glass vessel, the cover of which is provided with a through-bore such that the measuring head of a hygrometer is introduced therein. After about a minute, depending on the construction of the device, the measured value can be read.

The further processing takes place, after longitudinal section, in punching devices or simply by transverse section. The sheet-like products produced preferably have a thickness of between 20 and 300 $\mu$m; their size may advantageously range from 0.5 to 12 cm$^2$. Subsequent packaging may take place singly or in a stack, for example in sealed pouches or dosage dispensers.

What is claimed is:

1. Process for production of a product in the form of a sheet containing a substance to be dispensed by migration thereof into an environment in which the sheet is in contact, the process comprising:

applying onto a surface of a substrate a coating of a spreadable solution, the coating having a smooth surface and the spreadable solution comprising at least one hydrophilic polymer in a solvent and the substance to be dispensed, the substrate having at least one rough surface and the spreadable solution being coated onto a rough surface of the substrate;

drying the coated substrate by contacting it with a stream of heated air until the equilibrium relative humidity of the coated substrate is 50 to 75%; and removing the dried coating from the substrate in the form of said sheet, one surface of said sheet being smooth and the other, opposite surface of said sheet being rough.

2. The process according to claim 1, wherein the coated substrate is dried until the equilibrium relative humidity is 60 to 68%.

3. The process according to claim 1 or 2, wherein the drying is conducted in three stages, the heated air in a first stage having a temperature of 30 to 50° C., in a second stage having a temperature of 35 to 80° C., and in a third stage having a temperature of 25 to 50° C. and the temperature of the second stage is higher than the temperature of the first stage and the temperature of the third stage is lower than the temperature of the second stage.

4. The process according to claim 1, wherein the substrate comprises a thermoplastic polymer selected from the group consisting of polypropylene, polyethylene, polyethyleneterephthalate, polycarbonate, at least two polymers including at least one of the foregoing polymers laminated to each other, and paper coated with polyethylene.

5. The process according to claim 1, wherein the hydrophilic polymer is selected from the group consisting of starch and its derivatives, agar-agar, gelatine, cellulose and its derivatives, alginic acid, galactoglucomannane, carrageen, pullulan and other glucanes, dextrane, polyvinylpyrrolidone, polyvinylalcohol and polyacrylic acid homopolymers and copolymers.

6. The process according to claim 4, wherein the substrate comprises paper coated with polyethylene.

7. The process according to claim 5, wherein the hydrophilic polymer comprises pullulan.

8. The process according to claim 1, wherein the coating comprises additional hydrophilic substances of low molecular weight.

9. The process according to claim 8, wherein the hydrophilic substances of low molecular weight are selected from the group consisting of sugar, sugar alcohols, sugar substitutes, organic acids and polyethylene glycol.

10. The process according to claim 1, wherein the substance to be dispensed is selected from the group consisting of pharmaceutical agents, cosmetic agents, dietary supplement, colors, diagnostic agents, scents and flavors.

11. The process according to claim 10, wherein the substance to be dispensed comprises a flavor.

12. The process according to claim 1, wherein the coating comprises at least one substance selected from the group consisting of carbonates, phosphates, silicates and sulfates of alkaline earth metals, zinc oxide, titanium dioxide, other pigments, talcum, lactose, cyclodextrines, starch and derivatives of starch.

* * * * *